(12) United States Patent
Peura et al.

(10) Patent No.: US 9,359,590 B2
(45) Date of Patent: Jun. 7, 2016

(54) DERIVATION AND CULTURE OF HUMAN EMBRYO-DERIVED CELLS

(75) Inventors: Teija Tuulikki Peura, Yeronga (AU); Robert Paul Siebrand Jansen, Killara (AU)

(73) Assignee: SYDNEY IVF LIMITED, Sydney, New South Wales ( * ) Notice: Subject to any disclaimer, the term of this patent is extended or adjusted under 35 U.S.C. 154(b) by 1310 days.

(21) Appl. No.: 11/667,865

(22) PCT Filed: Nov. 16, 2005

(86) PCT No.: PCT/AU2005/001740
§ 371 (c)(1),
(2), (4) Date: May 16, 2007

(87) PCT Pub. No.: WO2006/053378
PCT Pub. Date: May 26, 2006

(65) Prior Publication Data
US 2008/0050813 A1    Feb. 28, 2008

(30) Foreign Application Priority Data

Nov. 16, 2004 (AU) ............................... 2004906554

(51) Int. Cl.
*C12N 5/00* (2006.01)
*C12N 5/073* (2010.01)
*C12N 5/0735* (2010.01)
*A61K 35/28* (2015.01)

(52) U.S. Cl.
CPC ............ *C12N 5/0604* (2013.01); *C12N 5/0606* (2013.01); *A61K 35/28* (2013.01)

(58) Field of Classification Search
CPC ..... A61K 35/28; A61K 8/982; C12N 5/0606; C12N 2500/02; C12N 2500/99; C12N 5/0607; C12N 5/0673; C12N 2502/02; C12N 5/0696
See application file for complete search history.

(56) References Cited

U.S. PATENT DOCUMENTS

| 5,843,780 A * | 12/1998 | Thomson ...................... 435/363 |
| 2004/0224401 A1 | 11/2004 | Ludwig et al. |
| 2005/0155099 A1 | 7/2005 | Rothenberg et al. |

OTHER PUBLICATIONS

Ezashi et al., Low $O_2$ tensions and the prevention of differentiation of hES cells. *Proc. Natl. Acad. Sci. USA* 102(13): 4783-4788 (2005).
Dumoulin et al., Effect of oxygen concentration on human in-vitro fertilization and embryo culture. *Human Reprod.* 14(2):465-469 (1999).

* cited by examiner

*Primary Examiner* — Blaine Lankford
(74) *Attorney, Agent, or Firm* — Wenderoth, Lind & Ponack, L.L.P.

(57) ABSTRACT

The present invention concerns methods for deriving and culturing embryonic cells and in particular to methods for maintaining the undifferentiated state of stems cells and cell lines in culture. The invention also concerns cells and cell lines derived by the methods of the invention.

3 Claims, 4 Drawing Sheets

DERIVATION AND CULTURE OF HUMAN EMBRYO-DERIVED CELLS

FIELD OF THE INVENTION

The present invention relates to the improvements in derivation/culture of embryo-derived cells or cell lines and, derivation/culture of human embryonic stem cells. More particularly the present invention relates to methods of culturing and maintaining embryo-derived cells in an undifferentiated state.

BACKGROUND OF THE INVENTION

Human Embryonic Stem Cells and their Derivation

Embryonic stem cells are undifferentiated cells that can grow in in vitro culture conditions, while retaining their capability to differentiate into specialized cell types having particular functions. Over the last few decades there has been a great interest in isolation and culture of human embryonic stem cells (hES-cells), as such cells can potentially provide a supply of readily available differentiated cells and tissues of all types to be used for therapeutic purposes in cell transplantation and gene therapy in humans, as well as for other medical uses such as drug discovery.

Early work on embryonic stem cells was done in mice (reviewed in Robertson, 1997; Pedersen, 1994). Current definition of both mouse and human embryonic stem cells includes the requirements for them to be capable of indefinite proliferation in vitro in an undifferentiated state, to retain a normal karyotype and to retain the potential to differentiate to derivatives of all three embryonic germ layers (endoderm, mesoderm, and ectoderm).

Methods for isolating and growing primordial stem cells (consisting of stem cells derived from both inner cell masses of embryos and from germ-cells of fetuses) from non-human primates and humans have been described previously in several publications (reviewed by Pedersen, 1999). A few of the seminal publications in this area are Thomson et al. (1995) (describing procedures for isolating Rhesus monkey primordial stem cells) and Thomson at al. (1998) (describing procedures for isolating human embryonic stem cell lines). Production of a new hES-cell line is called derivation. Once the population of undifferentiated cells has been derived from one embryo, they can be propagated indefinitely to yield unlimited numbers of cells that can be frozen and thawed or continuously cultured for several hundreds of cell divisions without the cells losing their ability to grow. At this stage it is called cell line. However, in order to maintain the undifferentiated state in culture, the calls need to be selected and passaged frequently to avoid the spontaneous differentiation otherwise taking place in growing colonies.

The source of hES-cell lines is excess human embryos donated for research by couples that have completed their fertility treatment and no longer need their embryos. In addition, embryos deemed to be unsuitable for clinical use due to poor viability or identified abnormalities, or even embryos specifically created for this purpose (under certain legislations) can be used. At a blastocyst stage, 5 or 6 days after fertilisation, the embryo consists of two distinctive cell populations; inner cell mass (ICM) cells and trophectodermal (TE) cells. Derivation of new hES-cell lines is based on culturing whole ICMs or cells thereof on a feeder cell layer. These cells are usually isolated from surrounding TE-cells by immunosurgery, although whole embryos can also be directly plated on feeder cells, whereby ICM-cells emerge from surrounding TE-cells during the course of culture. Earlier stage embryos can also be used, but the underlying principle remains the same: stem cells are derived from pluripotent undifferentiated cells within an embryo. The efficiency of hES-cell line derivation varies vastly between different laboratories, depending on isolation conditions, experience of the group and the quality of the embryos used. However, as the number of embryos donated for this purpose is usually limited, little experimentation has been conducted in this area and groups tend to use the methods originally employed with perhaps only slight variations. The success rates (percentage of successfully derived hES-cell lines per embryo used) vary from as low as 5% (Cowan et al. 2004) to 50% (Reubinoff et al. 2000). However, the comparison of success rates between groups is quite difficult because of the differences with respect to how the groups report their data; per cleavage-stage embryo or per blastocyst used, per total number of embryos entered into the program or per successfully plated blastocyst or ICM and so-forth.

So far the concerns about hES-cell line derivation efficiency have been mainly due to attempts to minimize the number of embryos needed. However, recent attention has been directed towards derivation of hES-cells from particular, individual embryos, for example of those identified by pre-implantation genetic testing or diagnosis (together, "PGD") to carry a specific genetic defect or chromosomal abnormality (Amit et al. 2004b; Galat et al. 2004; Verlinsky et al. 2004). Also the use of somatic cell nuclear transfer techniques for generating embryos for stem cell derivation (Hwang et al. 2004, 2005) puts more emphasis on the need to optimize the efficiency of successful hES-cell line derivation.

Most of the reported hESC-derivations have been performed with blastocysts grown in routine clinical conditions, in a variety of different embryo culture media. As >90% of the IVF clinics, especially in United States, use standard cell culture atmosphere of 5% $CO_2$ in air for culture, it is safe to assume that by far most hESC-derivations have been done with embryos produced in these conditions.

Production of Embryo Outgrowths and Other Undefined Embryo-Derived Cell Lines

Currently it is not possible to culture mammalian embryos in in vitro conditions much beyond the advanced blastocyst stage (in humans until day 8 or 9 of development) without embryos losing their identity as an embryo and their subsequent developmental potential to form a fetus. However, embryos or embryonic cells cultured for extended periods in vitro do have the capability to divide and grow into undefined cell populations (Hogan et al. 1994; Flechon et al. 1995; van Stekelenburg-Hamers et al. 1995; Tanaka et al. 1998; Talbot et al 2000; Leoni et al. 2000; Shimada et al. 2001; AlBadr & Handyside 2003). The acquisition of this kind of embryo-derived cell lines or outgrowths has important applications for diagnostic and research applications in the general field of in vitro fertilization and related assisted reproductive technologies (ART). The major restriction of any PGD-analysis is the limited number of cells available for analysis, combined with the uncertainty about how representative those few cells are for the embryo as a whole. Clinically and diagnostically, PGD analysis able to be performed on an unlimited number of cells derived from one embryo would offer improved accuracy and/or greater flexibility over the current analysis methods. A significant research application for such embryo-derived cells would be to use them for re-analysis in the course of development of new PGD-analysis methods, providing thereby the possibility to confirm an analysis made with a new method involving one or a few cells with a proven and tested method that requires many cells, and thereby constituting a valuable tool for refining PGD-methods.

Although there have been a few reports detailing derivation of trophectodermal or other, undefined embryo-derived cell lines from animal embryos (Hogan et al, 1994; Flechon et al. 1995; van Stekelenburg-Hamers et al. 1995; Tanaka et al. 1998; Talbot et al 2000; Leoni et al. 2000; Shimada et al. 2001; AlBadr & Handyside 2003), no successful derivations of non-pluripotent cell lines (such as trophoblast stem cell lines) have been reported from human embryos, and neither pluripotent nor non-pluripotent cell lines have been successfully derived from embryo biopsies, despite some attempts (Geber et al. 1995; Geber & Sampaio 1999). Recent success in producing embryonic stem cell line from a biopsied blastomere in mouse (Chung at al. 2005) suggests that in certain cases this may be possible, but the methods used involve aggregation of blastomere with an existing stem cell line, thus creating mosaic cell lines. Whether these methods would be applicable in generating human embryonic stem cell lines is not yet known. Nevertheless, due to complications owing to mosaicism, these methods may not be readily suitable in clinical situations for evaluation of particular embryos.

Culture of Human Embryonic Stem Cell Lines

The usual method for "maintenance" culture of human embryonic stem cells after the initial derivation phase is to grow them on a layer of somatic feeder cells, such as foetal fibroblasts. Cells can be passaged (moved from an old feeder cell dish to a now dish) manually by cutting colonies into small pieces by a blade or glass pipette, teasing the fragments away from the bottom of the dish and transferring them to a new dish ("mechanical" or "manual passaging"). Another method of passaging involves the use of enzymes or enzyme-free buffer solutions to disperse colonies into cell clumps or a single cell suspension and transfer all or some of these cells into new dishes ("bulk passaging"). It is also possible to grow hES-cells without feeder cells on dishes coated with gelatin or extracellular matrix and using either media conditioned by feeder cells or a defined media with exogenous growth factors (Xu, C. et al. 2001, Nat Biotechnol 19:971; Bodnar et al., 2004, U.S. Pat. No. 6,800,480).

The requirement for passaging of hES-cells is not driven only by the need to chance them to a fresh batch of feeder cells, but due to their propensity to spontaneously differentiate if the colonies are left to grow too large. Even in feeder free conditions regular passage is required to prevent differentiation. Maintaining stem cells in undifferentiated stage is controlled by a complicated network of signal transduction pathways, which in turn are affected by culture conditions and cellular interactions within a colony of stem cells. The presence of even small numbers of differentiated cells and their interaction with neighbouring undifferentiated cells can play an important role in determining the fate of the adjacent cells.

The area of improvement that has received most attention lately has been the attempts to reduce reliance on animal-derived cells and any other animal or bacteria-derived biological products in culture, in favour of more defined culture conditions (Amit et al. 2004a). Not much progress has been made in the field of improving cell culture conditions in the more "traditional" culture systems (including culture on feeder cells).

Culture of Embryo Outgrowths and Undefined Embryo-Derived Cell Lines

Because only a few of the successful cases have been reported in the literature, and employing a variety of species, there is no such thing as "a routine culture method" for other embryo derived outgrowths and cell lines. Many of the approaches have utilized very similar culture conditions as used for stem cells, including the use of feeder cells (Tanaka et al. 1998; Talbot et al. 2000). However, feeder-free culture systems have also been used (Leoni et al. 2000). The best culture conditions have probably not yet been defined, but the culture on feeder cells still is the most used approach.

Spontaneous Differentiation of Human Embryonic Stem Cell Lines

Human embryonic stem cells in culture differentiate spontaneously after a prolonged culture or if cultured in suboptimal culture conditions. The first recognisable sign of differentiation is the upregulation and expression of markers not present in undifferentiated populations. The exact type of markers depends on towards which cell lineage the differentiation is progressing (e.g. TDGF1, AP-2, MSX-2 (reviewed by Rao & Stice, 2004)

The Role of Oxygen Tension

All published initial derivations of human embryonic stem cells, trophectodermal stem cells and even all the attempts to grow embryo biopsies in order to generate embryo-derived cell types, have utilized the traditional cell culture gas atmosphere of approx. 5% $CO_2$ in air. These same conditions have also been used universally for the subsequent culture of hES-cells. Likewise, most IVF clinics still rely on traditional high oxygen atmosphere in their embryos culture, although change to reduced oxygen culture is slowly gathering momentum especially in Australia and Europe.

Studies on embryos of various species have suggested that early pre-implantation embryo development is improved in an atmosphere of low oxygen, usually in a gas mixture of 5% $CO_2$, 5% $O_2$ and 90% $N_2$ (Catt & Henman 2000; Orsi & Leese 2001). Although embryo-derived cell lines quickly lose their original "embryonic development program" (the genetic program controlling early embryo development), to be replaced by another type of developmental control, it is proposed herein that the two developmental patterns have enough in common to justify the hypothesis that the derivation and culture of embryo-derived cell lines (including, but not exclusive only to bona fide human embryonic stem cells) will be improved in low oxygen culture conditions. The process can be improved even further, as described herein, by utilizing a system where both the production of embryos (blastocysts or earlier stages), as well as derivation and subsequent culture of embryonic stem cell lines is performed in low oxygen culture conditions.

Thus there is still a need for novel methods of increasing the growth rate and/or reducing the spontaneously occurring differentiation of hES-cells in culture thereby increasing the potential for utilization of these cells Thus, it is an object of the present invention to provide improved methods for derivation and/or culture of embryonic stem cells and cell lines as well as other types of embryo-derived cells and cell lines.

SUMMARY OF THE INVENTION

According to a first aspect the invention provides a method of maintaining the undifferentiated state of an embryonic cell or embryonic cell line in culture comprising the step of culturing the embryo-derived cells or embryo-derived cell lines under conditions of low oxygen tension.

According to a second aspect the invention provides a method of supporting the proliferation of undifferentiated embryonic cell or embryonic cell line in culture comprising the step of culturing the embryo-derived cells or embryo-derived call lines under conditions of low oxygen tension.

According to a third aspect the invention provides a method for large scale production of undifferentiated embryonic cells comprising the step of culturing embryo-derived cells or embryo-derived cell lines under conditions of low oxygen tension.

According to a fourth aspect the invention provides a method of derivation of embryo-derived cells or embryo-derived cell lines comprising the steps of:

a) culturing an embryo under low oxygen tension conditions for a time sufficient to produce embryonic cell-like outgrowths, and b) isolating and culturing the embryonic cell-like outgrowths under low oxygen tension conditions to obtain embryo-derived cells or embryo-derived cell lines.

According to a fifth aspect the invention provides a method of derivation of embryo-derived cells or embryo-derived cell lines comprising the steps of:

a) incubating a putative zygote in a culture medium under low oxygen tension conditions to derive an embryo, b) culturing the embryo obtained in step a) under low oxygen tension conditions for a time sufficient to produce embryonic cell-like outgrowths, and c) isolating and culturing the embryonic cell-like outgrowths under low oxygen tension conditions to obtain embryo-derived cells or embryo-derived cell lines.

In relation to the methods of aspects four and five, the step of preparation/culturing of the zygote and/or embryo, prior to derivation, isolation or culture of embryonic cells there from, can be conducted under normal (atmospheric) oxygen conditions.

Preferably the embryo-derived cell or embryo-derived cell line is a stem call or stem cell line.

According to a sixth aspect the invention provides an embryonic cell or embryonic cell line obtained according to the method of any one of the aspects described above.

Preferably the call or cell line is a bona fide human embryonic stem cell or call line however it will be understood that the method of the present invention may be used for derivation and/or culture of embryonic stem cells from any mammalian species. Even more preferred is an embryonic stem cell or cell line derived from a human blastocyst.

In other embodiments of the present invention methods are provided for maintaining and specifically increasing the proportion of undifferentiated cells within an embryonic stem cell colony or stem cell colonies comprising the step of culturing the embryo-derived cells or cell lines under conditions of low oxygen tension.

According to a seventh aspect the invention provides the use of a cell or cell line according to the sixth aspect, or a cell or cell line derived by a method of any one of the previous aspects for pre-implantation genetic testing, or diagnosis of a genetic defect or chromosomal abnormality.

According to an eighth aspect the invention provides the use of a cell or cell line according to the sixth aspect, or a cell or cell line derived by a method of any one of the previous aspects, for chromosomal karyotyping.

The cells or cell lines of the present invention may also be characterized at the DNA, RNA and/or protein level by techniques well known in the art. Various known differentiation markers can be used to monitor the cells during growth and subculture, to assess and confirm the undifferentiated state of the cells.

It will be understood by those skilled in the art that the cells or cell lines derived by the methods of the present invention will not necessarily be a pure culture of undifferentiated cells and that certain content of differentiated cells will be present. However, the methods of the present invention provide cultures of cells which are enriched or contain a greater proportion of undifferentiated cells than cultures obtained by conventional methods using standard (atmospheric) oxygen conditions. Further, the methods of the present invention are suitable for large scale and/or automated production of undifferentiated cells.

The term "low oxygen tension", as used in the context of the present invention, includes in its scope culture conditions which make use of oxygen levels that are lower than those normally-used for culturing cells in vitro, namely less than about 20% $O_2$. Preferred $O_2$ concentration used in the present invention is about 5% $O_2$.

The term "embryo" as used in the context of the present invention is intended to include in its scope the various developmental stages of the embryo, including the blastocyst stage as well as the earlier morula stage. On occasions throughout the text the terms "embryo" and "blastocyst" are used interchangeably but from the description provided it will be clear to those skilled in the art what is meant by these terms and their scope.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

DESCRIPTION OF THE PREFERRED EMBODIMENT

Figure 1:
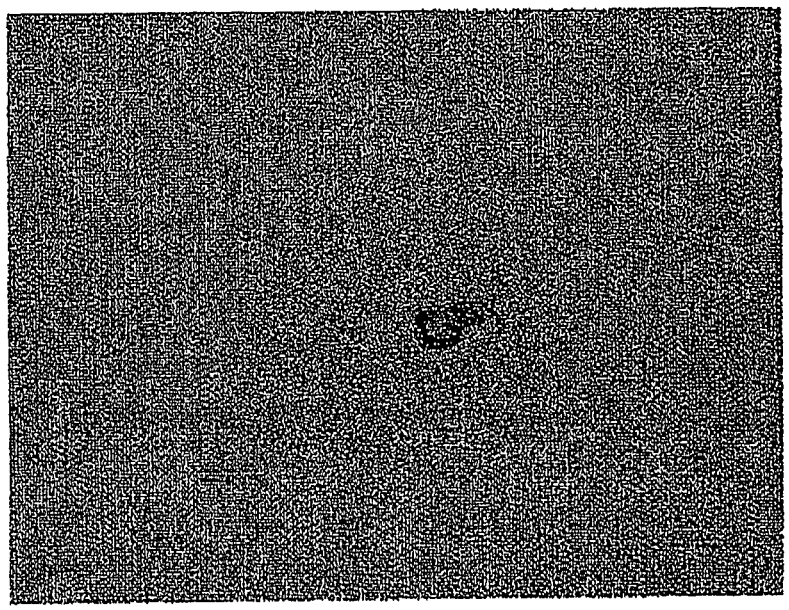
FIG. 1. Human blastocyst derived embryonic stem cell line 24 days after the initial plating at passage 2
Figure 2A:
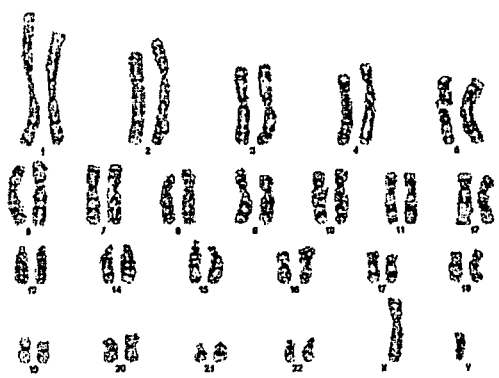
FIG. 2. a) Normal karyotype of an embryo-derived cell line b) Abnormal karyotype of an embryo-derived cell line exhibiting [46,XX,+16] (female trisomy–16)
Figure 2B:
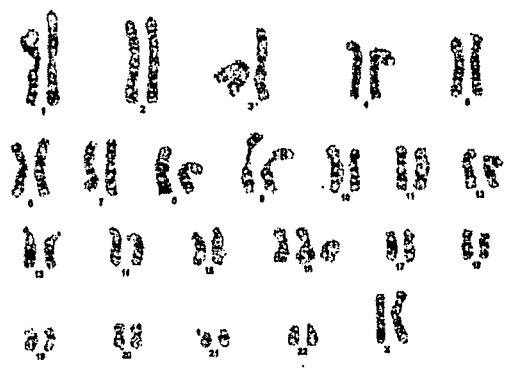

The present invention is based on a surprising finding that culturing human embryo-derived cells under low oxygen conditions preferentially enhances the growth of undifferentiated cells. This observation enabled the development of methods, as described herein, particularly for large-scale production of human embryonic stem (hES) cells and cell linens and their maintenance.

As mentioned earlier, human embryonic stem cells in culture differentiate spontaneously, thus limiting quantities of undifferentiated cells that can be obtained for diagnostic and other uses. Maintenance of the undifferentiated state of the cells requires careful and labour intensive handling, which further limits the potential for derivation of larger quantities of hES cells or successful and economic maintenance of such cells.

Derivation and culturing of human embryo-derived cells and cell lines under low oxygen conditions enables use of passaging and other cell culture techniques which are less labour intensive and lend themselves to large scale and/or automated production and maintenance of undifferentiated hES cells and cell lines.

Typically, when the embryo-derived cells are cultured at levels of oxygen below atmospheric, eg. about 5% $O_2$, the undifferentiated cells grow faster than the differentiated cells thus diluting out the effect of differentiated cell populations in that passage and when/if carried on to the successive subculture. Importantly, this characteristic of the culture conditions and the undifferentiated cells minimises and even obviates the need to visually select the undifferentiated colonies of cells, although this can still be done if preferred, and enables use of enzyme-based techniques of passaging the calls. This in turn minimises labour and enables the methods to be automated or at least be applicable to large scale production and maintenance of hES cells and cell lines.

Accordingly, for large scale production hES cells and cell lines can be cultured in individual or assemblies of large flasks, trays, roller bottles, carrier beads or the like and harvested or passaged as required by treating the culture surfaces with reagents (enzyme-containing or enzyme-free) which detach the cells and enables them to be washed, diluted as required and seeded into fresh culture vessels. It is clear that this process can be repeated numerous times with minimal involvement of manual and labour intensive selection techniques previously required while favouring the enrichment of undifferentiated cells with each successive passage.

EXAMPLES

Example 1

Embryo Production

The embryo production protocol follows Sydney IVF Embryology Laboratory ISO 9001 accredited protocols as routinely performed at Sydney IVF Ltd., 4 O'Connell St., Sydney, NSW 2000, Australia, and as described in McArthur et al. (2005) (incorporated by reference herein in its entirety.) Briefly, following the follicular aspiration of the patients treated with a standard superovulation treatment, cumulus cell-oocyte complexes are immediately washed in SIVF Fertilisation Medium. Oocytes are then incubated in 30 µl drops of same medium in 4-well dishes for 3 h, before adding spermatozoa at a concentration of 80,000-150,000/ml. The spermatozoa are prepared by 20 min centrifugation at 300 g in 40 and 80% PureSperm®-gradient according to the manufacturers specifications (Nidacon Int., Gothenburg, Sweden). After 1 h co-incubation, oocytes are cleaned of loose cumulus-cells by pipetting and transferred to clean Fertilization Medium drops. After overnight incubation putative zygotes are completely cleaned of cumulus cells, checked for fertilization and transferred to 10 µl drops of SIVF Cleavage Medium for 3 days, followed by another 2 to 4 days of culture in SIVF Blastocyst Medium drops. All the used media are either made in-house, or ordered from the commercial distributor of Sydney IVF media, Cook®IVF (Eight Mile Plains, Queensland, Australia). All the incubations take place in the atmosphere of 6% $CO_2$, 5% $O_2$ and 89% $N_2$ at +37° C. in a K-MINC-1000 incubator (Cook®IVF).

Culture of embryo-derived cell lines or outgrowths for karyotyping purposes was usually started from fresh (non-frozen) embryos at Days 6, 7 or 8 after fertilisation, hESC-derivation was attempted either of fresh embryos or embryos that had been frozen when 5 or 6 days old and subsequently thawed and cultured for one more day in embryo culture media before used for stem cell derivation.

The culture system described above yields very good embryonic development rates, approx. 65-70% of fertilised embryos reaching the blastocyst stage. The quality of the clinically suitable blastocysts is good also as judged by the clinical pregnancy rates achieved, 57% of fresh transfers in the patient group <38 years. The good quality blastocysts produced with the combination of SIVF embryo culture media and culture in reduced oxygen atmosphere in MINC-incubators also improves the rate of hESC-derivation per individual embryo.

Example 2

Production of Embryo Outgrowths and Undefined Embryo-Derived Cell Lines

The embryos used for cell line derivations were poor quality embryos, not clinically suitable, created for the use in ART program. The likelihood of this type of embryo to establish a normal pregnancy or to survive the rigors of freezing and thawing is so low that following a normal clinical practice they will be discarded. The embryos were designated as "investigative embryos", since prior to their treatment, the patients had given consent allowing embryos designated to be discarded to be used for clinical studies pertinent to their individual cases. The main aim of the cultures was to obtain greater number of cells from these embryos for detailed karyotyping analysis to ascertain the occurrence and prevalence of any possible chromosomal anomalies.

The embryos were originally produced following the normal clinical procedures in the SIVF embryology laboratory, as described above in Example 1 and as described by Jansen et al. (2003) (incorporated by reference herein in its entirety). Good quality embryos were transferred to patients or frozen five or six days after fertilisation with the rest of the embryos clinically discarded. These were the embryos that were allocated for further embryo outgrowth cultures.

The cultures were performed using either whole embryos, embryos separated into two parts consisting of either distinctive trophectodermal (TE) cells or inner cell masses (ICMs), or in some cases, immunosurgically isolated (Solter & Knowles, 1975) ICIMs alone. The outer shell of the non-hatched embryos (zona pellucida) was removed with 2-3 min incubation in 0.4% pronase (Sigma Chemical Company, St. Louis, Mo., USA) in HEPES-buffered Dulbecco's Minimum Essential Medium (DMEM; Gibco BRL, Grand Island, N.Y.), followed by wash in DMEM-HEPES alone. If embryos had already spontaneously hatched out of their zonae, this step was omitted. The immunosurgery was performed by incubating embryos 50 min in anti-human serum (Sigma) diluted 1:5 with PBS, followed by 15 min incubation in Guinea Pig Complement (Sigma), also diluted 1:5 with PBS. The final separation of TE-ells from ICMs was done by mechanical pipetting. Dissection of blastocysts to two parts was performed by manually cutting the embryo on a petri dish in a DMEM-culture medium using an Ultra-Sharp Splitting Blade (AB Technologies, Pullman, Wash., USA). In some cases, both parts of the embryo were then transferred to same culture dish, whereas in some cases only the trophectodermal part was cultured in an attempt to study the feasibility of deriving cell lines from a trophectodermal biopsy alone, a technique developed for clinical purposes in the laboratories at Sydney IVF (de Boer et al. 2004, incorporated by reference herein in its entirety).

The feeder cells were either human neonatal foreskin fibroblasts or human fetal fibroblasts, frozen-thawed and cultured in 5% $CO_2$ at 37° C. degrees in a regular incubator. The foreskin fibroblast cell line was kindly donated by North Shore Hospital, Sydney, NSW, and human fetal fibroblasts were either in-house derived from tissue samples obtained from a partner clinic in Czech Republic, or purchased from ATCC (American Tissue Type Collection, Manassas, Va., USA). The feeder cell dishes were prepared by inactivating fibroblast cultures between passages 4 to 10 by 10 µg/ml mitomycin for 2.5-3 h, followed by trypsinisation and plating on culture dishes at a density of either $70 \times 10^3$ or $25 \times 10^3$ cells/$cm^2$. The feeder cell culture medium was DMEM with the addition of glutamine, penicillin, streptomycin, MEM-amino acids, sodium pyruvate and 10% Fetal Calf Serum (FCS). The feeder cells were established in either 1 ml volumes in 1-well organ culture dishes or Nunc 4-well dishes (Nunclon, Roskilde, Denmark), and in some cases in 20 μl drops under oil in Nunc-dishes. Feeder cell dishes were kept in a regular incubator until used within a week. The outgrowth medium was identical to feeder cell medium except for the addition of β-mercaptoethanol and basic Fibroblast Growth Factor (bFGF) (Sigma), and replacement of 10% FCS with 20% of Knock-Out Serum Replacement (KSR) (Gibco BRL).

The gas atmosphere of the initial establishment period of the cultures was either 5% $CO_2$ in air (standard oxygen) in a regular cell culture incubator or 6% $CO_2$, 5% $O_2$ and 89% $N_2$ (low oxygen) in K-MINC-1000 incubator.

In each scenario, the initial period of outgrowth lasted between 4 to 14 days, after which time all successful outgrowths were passaged to new dishes. Passaging was done manually using a metal blade to cut outgrowths into several fragments and transferring them into new dishes with a pipette. As long as any cell division and outgrowth formation was observed, passages were continued in 7-10 day intervals until enough cells were generated for karyotype analysis, usually equivalent to three to five 1-well dishes. Getting this many cells could take anywhere between 4 and 11 passages or 3 to 8 weeks, depending on the growth characteristics of the individual outgrowths.

Figure 3:
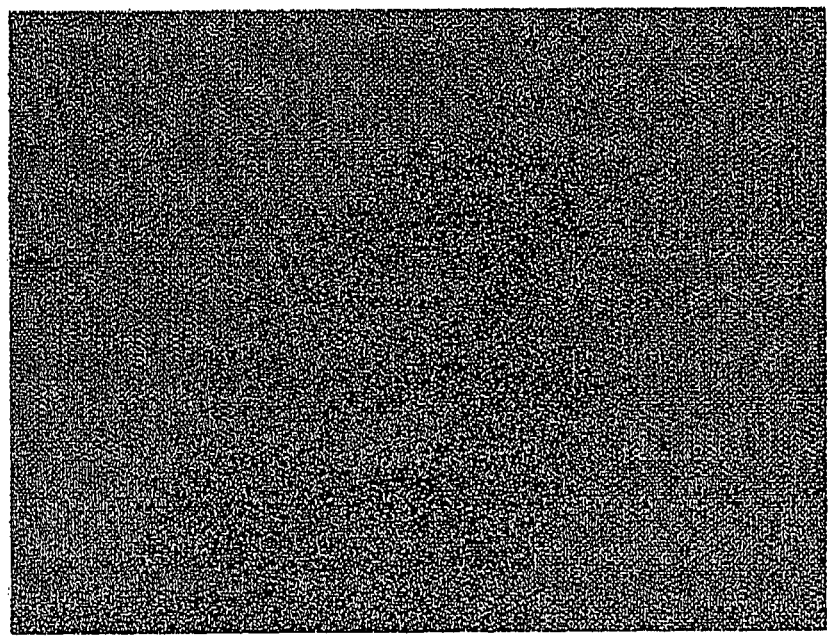
FIG. 3. Human embryonic stem cell line 'SIVF01' after 63 passages in low oxygen atmosphere

Total of 83 cultures were initiated from 176 discarded embryos in one study. Only seven cultures in this study could be cultured to the stage where adequate numbers for proper karyotyping could be obtained, representing 8.4% per initiated culture and 4.0% per individual embryo. All these cell lines were subsequently karyotyped using Sydney IVF Genetics ISO 9001 accredited cytogenetics protocols as routinely performed at Sydney IVF Ltd., 4 O'Connell St., Sydney, NSW 2000, Australia. Karyotypes revealed mainly normal [46, XX] or [46, XY] karyotypes, but also some aneuploidies were observed, e.g. chromosome 16 trisomy [46,XX, +16] (FIG. 3). Success rate in low oxygen atmosphere was twice as high as in standard oxygen (12.1 vs. 6.0%) (Table 1).

TABLE 1

Numbers of successful embryo-derived and karyotyped cell lines produced using standard vs. low oxygen atmosphere

| Oxygen level | Whole embryo culture | Bisection# | Total |
|---|---|---|---|
| Standard $O_2$ | 3/40 (7.5%) | 0/10 (0%) | 3/50 (6.0%) |
| Low $O_2$ | 3/20 (15.0%) | 1/13 (7.7%) | 4/33 (12.1%) |
| Total | 6/60 (10.0%) | 1/23 (4.3%) | 7/83 (8.4%) | both parts of the embryo cultured in same dish

Example 3

Culture of Embryo Derived Outgrowths and Cell Lines in Standard vs. Low Oxygen

The initial experiments comparing the culture of cells in standard vs. low oxygen culture conditions consisted of six replicates performed with five different outgrowths between passages 4 and 8. The experimental design consisted of measuring the size ($mm^2$) of several cell colonies with the help of the objective graticule. The colonies were then cut into 2 to 6 equal size pieces with a glass pipette (number depending on the original size of the colony) and pieces distributed equally to new feeder dishes. The dishes were cultured in regular incubator or in K-MINC (standard vs. low oxygen) for seven days, after which the colony sizes were measured and colonies passaged again as previously described, for the additional seven days of culture. The culture experiment was finished at Day 14 of the culture with the final colony size measurements. The actual overall growth rates of the colonies (the area of the colonies at Day 0 deducted from the area of the colonies at Day 7 or Day 14) between the two groups were compared using Mann-Whitney non-parametric test in Graph Pad Prism statistical program.

Results showed that hESC colonies grew significantly larger in low oxygen atmosphere. The overall total sizes of the colonies increased from 35.2 $mm^2$ in both groups at the beginning of the experiment to 97.6 and 62.4 $mm^2$ by Day 7 and to 352.9 and 145.3 $mm^2$ by Day 14 in low and standard oxygen groups, respectively (Table 2). Although there were no statistically significant differences in the mean growth during just 7 days of culture, during the 14 days of culture the difference was significant in favour of low oxygen culture (Table 2). When specifically looking at the growth rate of undifferentiated portion of the colonies, it was observed that low oxygen atmosphere in particular increased the proliferation of undifferentiated cells (Table 3.).

TABLE 2

Sizes and growth rates of embryo-derived cell colonies in standard vs. low oxygen atmosphere over a two-week culture period (data compiled from 6 culture experiments with 5 different embryo outgrowths)

| | STANDARD $O_2$ | LOW $O_2$ |
|---|---|---|
| | Total area of colonies $mm^2$ (mean size) (range) | |
| Day 0 | 35.2 (5.9) (4.1-7.2) | 35.2 (5.9) (4.1-7.2) |
| Day 7 | 62.4 (10.4) (4.4-23.) | 97.6 (16.3) (14.7-26.6) |
| Day 14 | 145.3 (24.2) (10.5-32.1) | 352.9 (58.8) (25.9-113.7) |
| | Mean growth of colonies ± SEM ($mm^2$) | |
| Day 0 to Day 7 | 4.53 ± 2.72[a] | 10.40 ± 3.58[a] |
| Day 7 to Day 14 | 13.82 ± 3.09[a] | 42.56 ± 11.63[a] |
| Day 0 to Day 14 | 18.35 ± 3.60[b] | 52.96 ± 12.90[a] |

[a,b]Different superscripts within a row denote statistically significant difference ($p < 0.05_{[42]}$)

TABLE 3

Growth of undifferentiated cells in embryo-derived cell colonies in standard vs. low oxygen atmosphere over a two-week culture period (data compiled from 6 culture experiments with 5 different embryo outgrowths)

| | Undifferentiated growth (mean ± SEM) ($mm^2$) | |
|---|---|---|
| | STANDARD $O_2$ | LOW $O_2$ |
| Day 0 to Day 7 | 1.58 ± 1.375[a] | 6.00 ± 2.419[a] |
| Day 7 to Day 14 | 10.75 ± 1.144[a] | 36.44 ± 8.472[b] |
| Day 0 to Day 14 | 12.33 ± 2.262[a] | 42.43 ± 10.29[b] |

Different superscripts within a row denote statistically significant difference:
[a,b]$p < 0.001$ Example 4

Human Embryonic Stem Cell Line Derivation

Human embryonic stem cell derivation work was approved by the National Health and Medicine Council's Licensing Committee, and the work conducted according to the *Research Involving Human Embryos Act* (Cth) 2002. The human embryos used were excess ART-embryos donated to research through the informed consent process by the patients. Two Day 5 and one Day a glycerolfrozen blastocysts from the same patient were thawed following Sydney IVF Embryology laboratory ISO 9001 accredited protocols, briefly as follows: embryo straws were thawed first in air for 30 sec, then in +30° C. water bath for 30-40 sec, after which the straws were cut open and embryos expelled into a dish. They were then incubated 10 minutes each in 0.5, 0.2 and 0.1 M sucrose-solution; prepared in SIVF CryoBuffer. Finally they were transferred into SIVF Blastocyst medium in K-MINC-1000-incubator (low oxygen atmosphere). After overnight culture, the zonae of the two surviving blastocysts were removed with 0.4% pronase. Embryos were plated on 1-well organ culture dishes containing 200 000 mitomycin-treated human fetal fibroblasts in DMEM/F12-medium supplemented with 20% FCS, 0.1 mM mercaptoethanol and 4 ng/ml bFGF. Medium was changed every second day, and fresh bFGF was added to cultures every day. One embryo was cultured in K-MINC-1000-incubator in a low oxygen atmosphere, the other in a regular incubator in a standard oxygen atmosphere, both at 37° C. Resulting outgrowths were first passaged 4-7 days later and since then, every week.

The embryo grown in low oxygen showed typical hES-cell like outgrowths after two passages by Day 16, and subsequent passages confirmed the existence of actively growing hES-cell like population of cells (FIG. 1). The embryo grown in standard oxygen did not display typical hES-morphology at any stage of the culture, and after over two months of culture it was eventually discarded after exhibiting only very restricted and diminished cell growth.

In another attempt, two Day 5 blastocysts from a different patient were thawed and cultured overnight as described. The only surviving blastocysts was plated as above and cultured in standard oxygen conditions. This embryo did not display any hES-like growth characteristics and was likewise discarded after approximately two months.

The cells from the one thriving hES-cell like culture have been subsequently characterized and identified to be true human embryonic stem cells, and the cell line has consequently been named "SIVF01". The characterization was done by Immunocytochemical analysis, which showed cells to be positive for human pluripotent embryonic stem cell specific markers SSEA-4, Tra-1-60 and Oct4 as well as for alkaline phosphatase, and negative for marker SSEA-1. SIVF01 has also been karyotyped at various passages (3, 30, 37, 38, 63), always revealing normal 46XX karyotype. Subsequent differentiation studies have shown these cells to be capable for differentiation in vitro to embryoid bodies and to cardiomyocytes. They have also been tested for in vivo differentiation by injection to SCID (immunodeficient) mice, where they were found to form teratomas containing tissues of the three embryonic germ layers.

In addition to routine ongoing culture of SIVF01 in low oxygen atmosphere, a subline was separated at P. 27 and cultured in standard oxygen atmosphere for over 11 months (>40 passages) parallel to the line kept in low oxygen. This subline has been subsequently characterized and karyotyped (at passages 38 and 63), and shown to be identical in performance to the line grown in low oxygen, further confirming the suitability of low oxygen conditions to hESC culture.

SIVF01 has been passaged continuously at least up and beyond P. 70. It has also been cryopreserved at various passages using slightly modified Open Pulled Straw vitrification method (Vajta et al. 1998, Reubinoff et al. 2001). Briefly, undifferentiated colonies were cut into pieces (approx. 0.8×0.8 $mm^2$), equilibrated few minutes in warm (37° C.) bench-medium of DMEM-Hepes+20% FCS, 20 to 30 sec in warm bench medium containing 10% Ethylene Glycol and 10% DMSO (v/v) and finally 20-30 sac in warm bench medium containing 20% Ethylene Glycol, 20% DMSO (v/v) and 0.5 M sucrose, while being loaded to open-ended OPS-straws (LEC-Instruments, Scoresby, VIC, Australia) in approx. 2 µl volume and plunged into liquid nitrogen. The straws were immediately inserted into 0.5 ml straws that were sealed with BD Seal Ease (Becton Dickinson, Franklin Lakes, N.J. USA), thus creating double-straw (Vajta et al. 1998) to avoid possibly cross-contamination in liquid nitrogen storage. Several straws have been subsequently warmed and and cultured to verify the viability of hESC colonies after vitrification, and in all cases found to survive and continue their undifferentiated growth at the manner equal to fresh cultures.

Example 5

Culture of Human Embryonic Stem Call Lines

The experiments comparing the culture of Sydney IVF derived hESC colonies (SIVF01) in standard vs. low oxygen culture conditions were performed identically to the experiments conducted with embryo derived outgrowths and cell lines, including the data collected regarding the proportions of undifferentiated vs. differentiated cells within the colonies. Experiments consisted of six replicates performed with hESC lines between passages 18 and 20. The experimental design was as described before for embryo derived outgrowths and cell lines, consisting of 14 day culture period with one passage at Day 7. The actual overall sizes of the colonies, as well as the sizes of undifferentiated parts of the colonies between the two groups were compared using unpaired t-test utilizing Graph Pad Prism statistical program.

Like with embryo-derived calls, hESC colonies grew more than twice in size in low oxygen atmosphere as compared with standard atmosphere. The overall total sizes of the colonies increased from 10.1 $mm^2$ in both groups at the beginning of the experiment to 40.5 and 77.7 $mm^2$ by Day 7 and to 183.0 and 419.3 $mm^2$ by Day 14 in standard and low oxygen groups, respectively (Table 4). Although the proportion of undifferentiated growth in colonies was slightly less at Day 7 in low oxygen group (94 vs 80% In standard vs. low), at day 14 the proportion of undifferentiated growth was identical between the two groups (83 vs. 84%, respectively). The temporary dip in undifferentiated growth was most likely the result of faster growth, as the bigger colonies grow, the quicker they start to differentiate. Both during the first 7 days and during the whole 14 days of culture, the mean growth of total colony size was likewise statistically significantly higher in low oxygen culture (Table 6). In addition, the overall increased growth of undifferentiated cells in low oxygen (Table 7.) suggests that the low oxygen conditions specifically favour proliferation of undifferentiated stem cells.

TABLE 4

Total growth rates of SIVF01-hESC colonies in standard vs. low oxygen atmosphere over a two-week culture period (data compiled from 6 culture experiments)

|  | STANDARD $O_2$ | LOW $O_2$ |
| --- | --- | --- |
|  | Total area of colonies $mm^2$ | |
| Day 0 | 10.1 | 10.1 |
| Day 7 | 40.5 | 77.7 |

TABLE 4-continued

Total growth rates of SIVF01-hESC colonies in standard vs. low oxygen atmosphere over a two-week culture period (data compiled from 6 culture experiments)

|  | STANDARD $O_2$ | LOW $O_2$ |
|---|---|---|
| Day 14 | 183.0 | 419.3 |
| | Undifferentiated area of colonies mm$^2$ (% of total size) | |
| Day 0 | 10.1 (100) | 10.1 (100) |
| Day 7 | 38.0 (94) | 62.5 (80) |
| Day 14 | 151.2 (83) | 351.1 (84) |
| | Mean total growth of colonies (mm$^2$) | |
| Day 0 to Day 7 | 5.08 ± 0.448[a] | 11.28 ± 0.938[c] |
| Day 7 to Day 14 | 23.75 ± 4.475[a] | 56.93 ± 1.467[c] |
| Day 0 to Day 14 | 28.82 ± 4.676[a] | 68.20 ± 1.241[c] |

Different superscripts within a row denote statistically significant difference:
[a,b] $p < 0.001$;
[a,c] $p < 0.005$

TABLE 5

Growth of undifferentiated cells of SIVF01-hESC colonies in standard vs. low oxygen atmosphere over a two-week culture period (data compiled from 6 culture experiments)

| | Undifferentiated growth (mean ± SEM) (mm$^2$) | |
|---|---|---|
| | STANDARD $O_2$ | LOW $O_2$ |
| Day 0 to Day 7 | 4.66 ± 0.491[a] | 8.74 ± 0.298[c] |
| Day 7 to Day 14 | 18.87 ± 3.375[a] | 48.10 ± 5.649[b] |
| Day 0 to Day 14 | 23.53 ± 3.630[a] | 56.85 ± 5.708[c] |

Different superscripts within a row denote statistically significant difference:
[a,b] $p < 0.001$;
[a,c] $p < 0.005$ Example 6

Derivation and Long Term Culture of Several Human Embryonic Stem Cell Lines in Reduced Oxygen Atmosphere Additional (in addition to Example 4) human embryonic stem cell line derivations were performed only in the low oxygen atmosphere, as our experiences had already proven it to be more efficient method than the culture in high oxygen, and using valuable human material in conditions known to be less than optimal would have been unethical.

The embryos in this study were donated by the patients undergoing IVF treatment combined with Preimplantation Genetic Diagnosis (PGD) analysis for aneuploidy detection. The inclusion of patients in the PGD-program was based on clinical evaluation and their past treatment history. All the couples signed informed consent to use embryos for this particular project. The used embryos were either aneuploid embryos identified through PGD, or poor quality embryos that were unsuitable for POD-analysis and were discarded as per routine clinical assessment. In some cases embryos of both types were obtained from a same patient.

The IVF procedures including fertilization either by oocyte-sperm co-incubation or intraoytoplasmic sperm injection (ICSI), and the culture of fertilised zygotes were essentially as described in Example 1. PGD-procedures were essentially performed as described by de Boer at al. (2004). Briefly, all embryos reaching 6-8-cell stage at Day 3 were subjected to laser-assisted hatching using Zilos-TK Infrared Laser (Hamilton Thorne Biosciences, Beverly, Mass., USA) and returned to culture. Partially hatched blastocysts were biopsied at Day 5 or 6 by aspirating the herniated portion of the trophectoderm into a pipette and separating it from the rest of the blastooysts with short laser bursts. The biopsy, consisting of 2 to 5 cells, was then processed for Fluorescence In Situ Hybridisation with fluorescence probes recognizing chromosomes 13, 18, 21 X and Y (Vysis Inc, Downers Grove, Ill., USA). The blastomeres were then examined by fluorescence microscope for detection of chromosome specific fluorescence signals. The results were obtained on the same day and karyotypically normal embryos were either transferred to patient or frozen for later transfers, and karyotypically abnormal embryos were allocated to stem cell derivation. Embryos deemed not suitable for biopsing on Day 5 or 6 based on their developmental stage and quality were also allocated to stem cell derivation on Day 6, 7 or 8.

The feeder cells were either in-house produced human fetal fibroblasts or commercially available human fetal fibroblasts (ATCC®, Manassas, Va., USA). The feeder cell dish preparation and the Feeder medium used were as described in Example 4. The stem cell medium was initially (for the first 8 platings) DMEM/F12 with 2 mM glutamine, 50 U/ml penicillin & 50 mg/ml streptomycin, 1× MEM-amino acids, 1% ITS-G, 0.1 mM β-mercaptoethanol and 20% FCS, and for the remaining 28 cases ft was KO-DMEM with the addition of 2 mM glutamine, 50 U/ml penicillin & 50 mg/ml streptomycin, 1× MEM-amino acids, 0.1 mM β-mercaptoethanol and 20% Knock-Out Serum Replacement (KSR). In both cases 4 ng/ml bFGF (Sigma) was added into media just before use. All cultures were performed in reduced oxygen atmosphere in K-MINC-1000 mini-incubators at +37° C.

Most of the embryos of good developmental quality were manually bisected using an EtOH sterilized Ultra-Sharp Splitting Blade to remove zone pellucida (if not fully hatched) and to separate ICM and the polar trophectoderm from mural trophectoderm, plating only the ICM-containing part to the feeder dish. In some cases poor quality embryos, not suitable for bisection, were plated whole after removal of zona pellucida either by 2 min incubation in 0.4% Pronase (Sigma) or mechanical cutting with a splitting blade. The complete media change or addition of fresh FGF was done on alternative days of culture. The first passage of ICM-outgrowth was performed 4-7 days after plating, and henceforth every 4 to 14 days until stable ES-like growth was observed. Passaging was done manually by cutting outgrowths with a splitting blade into 1 to 3 fragments and transferring them with a flame-pulled glass pipette to a fresh feeder dish. Once stable ES-like colonies had been established, passaging was done using a glass pipette both for cutting and transferring the colony fragments.

The resulting putative hESC-lines were expanded and passaged continuously, and cryopreserved at various passages using the vitrification method described in Example 4. Straws from each lines were subsequently warmed and cultured to verify the success of cryopreservation.

Characterisation of putative hESC lines was essentially as described in Example 4, including karyotype analysis, alkaline phosphatase staining, immunocytochemistry of undifferentiated colonies with specific markers, in vitro differentiation to embryoid bodies and their subsequent processing for immunohistochemistry using antibodies against markers for three embryonic germ layer cells. Two of the cell lines were also examined for teratoma formation in SCID (immunodeficient) mice.

A total of 36 cultures were set up with 41 embryos from 21 patients in this study (in five cultures two non-PGD analysed embryos were plated on a same culture dish). In thirty cultures at least one embryo plated, and total of 11 new hESC-lines were obtained (Table 8.).

Higher derivation success was achieved with PGD-analysed embryos than with non-PGD embryos (45 vs. 13%), which most likely is due to the generally better quality of the PGD-analysed embryos. At the time of plating, embryos were assessed based on a clinical blastocyst grading system utilized at Sydney IVF where grade 1=good, 2=fair and 3=poor. The distribution of embryos to quality grades 1, 2 and 3 was 44 and 13% for non-PGD embryos and 65, 30 and 5% for PGD-embryos. However, with non-PGD embryos cell lines were obtained at equal efficiency from grades 1 and 2 (1/7, 14%), and with PGD-embryos relatively more cell lines were obtained from grade 2 than from grade 1 (4/6, 67% and 5/13, 38, respectively).

TABLE 6

Embryonic stem cell line derivations of Preimplantation Genetic Diagnosis-analysed and non-analysed embryos, plated as whole embryos or after bisection

| PGD-status | Embryo manipulation | Embryo grade[1] | Cultures established (No. of embryos) | hESC-lines obtained (% of cultures) |
|---|---|---|---|---|
| Analysed | Total | | 20 (20) | 9 (45) |
| | Whole | 1 | 3 (3) | 1 (33) |
| | | 2 | 3 (3) | 2 (67) |
| | | 3 | 1 (1) | 0 (0) |
| | Bisected | 1 | 10 (10) | 4 (40) |
| | | 2 | 3 (3) | 2 (67) |
| | | 3 | — | — |
| Not analysed | Total | | 16 (22) | 2 (13) |
| | Whole | 1 | 4 (7) | 0 |
| | | 2 | 3 (4) | 1 (67) |
| | | 3 | 1 (1) | 0 |
| | Bisected | 1 | 3 (3) | 1 (67) |
| | | 2 | 4 (5) | 0 |
| | | 3 | 1 (2) | 0 |

[1] 1 = good, 2 = fair, 3 = poor

All eleven cell lines have been continuously passaged since their derivation, most advanced cultures being cultured at least up and beyond P. 60.

Karyotype analyses have been performed for one of the cell lines at passages 6, 29 and 55, and in all cases the same results were obtained. Six cell lines have been analysed twice, approximately in passages 5 and 28. Three more lines have been analysed once, at approx. passage 5. In all repeat analyses the results have been the same for each cell line. Overall, eight cell lines were karyotypically normal, X being female and Y male cell lines. Three aneuploid cell lines were detected: one female trisomy 16 (46XX,+16), one mosaic cell line contain normal female (46XX) and isochromosome 13 (46,XX,l(13)(q10)) and one male trisomy 5 (46 XY,+5) (FIG. 3). The trisomy-16 originated from an embryo that had been categorized as triploid in the original PGD-analysis, and two others from embryos categorized as "chaotic", i.e. one or more of the analysed cells of the PGD-biopsy had aneuploid number of chromosomes, however not necessarily similar aneuploidy in all cells.

All the hESC cultures, from derivation up to passage 60, have been successfully performed exclusively in low oxygen atmosphere, first in K-MINC-1000 incubators, later in a Heracell 150 multigas incubator (Kendro Laboratory Products, Hanau, Germany), which also utilises 6% $CO_2$, 5% $O_2$ and 89% $N_2$-atmosphere. This indicating that these conditions are eminently suitable for maintenance and expansion of human embryonic stem cells. Karyotyping results support the notion that low oxygen conditions support normal cell proliferation and maintenance. Likewise, derivation success of developmentally normal (i.e. embryos that were deemed suitable for PGD-analysis, as opposed to developmentally retarded deemed not suitable for PGD) embryos of 47% is very high, when compared with the several published success rates. For example van de Stolpe et al. (2005) utilised 22 blastocysts for one cell line, and Cowan et al. (2004) utilised total of 286 cleavage stage embryos and 58 blastocysts to yield 97 inner cell masses, resulting eventually to 17 cell lines.

Example 7

Large-Scale Derivation and Production of Human Embryonic Stem Cells for Therapeutical and/or Pharmacological Applications The initial embryo culture and hESC derivation was performed according the methods described in earlier examples. The methods described here relate to efficient and rapid culture and production of large numbers of hES cells of undifferentiated phenotype.

When at least one 1-well organ culture dish with one or more uniform hESC colonies has been established, subsequent passages are performed "in bulk" using preferentially enzymatic cell dissociation methods. The method of choice depends on the applications, for example whether the cell production requires the use of xeno-free (non animal-derived) products and conditions. If not, enzymes such as Collagenase Type IV or Trypsin (Sigma) can be used, whereas if xeno-free conditions are required, products like TrypLE Select (Invitrogen) or Cell Dissociation Solution (Sigma) can be utilized.

The culture media used for cell expansion are known hESC-culture media, for example KO-DMEM as described in previous examples (KO-DMEM with glutamine, penicillin & streptomycin, MEM-amino acids, β-mercaptoethanol, Knock-Out Serum Replacement and bFGF). The feeder cells are human fibroblasts inactivated by gamma-irradiation or Mitomycin C (Sigma) treatment and plated on suitable culture dishes or flasks. For the initial embryo culture and hESC-derivation period, 1-well organ culture dishes (Becton-Dickinson) are used, and for cell expansion period, T25, T75 and T175 culture flasks (Becton Dickinson). All cultures take place in the atmosphere of 6% $CO_2$, 5% $O_2$ and 89% $N_2$ at +37° C. in +37° C. in a multigas incubator (Heracell 150).

The bulk passaging methods, irrespective of the reagent used, require careful timing of passaging in order to achieve a meaningful expansion potential but also to avoid the presence of too many differentiated cells in the colonies. The optimum time for passaging is when colonies have grown as large as possible, but still remain as fully undifferentiated as possible. This is because with these methods there is no visual selection of only the undifferentiated parts of the colonies, but all the cells in the colony are carried on to the next passage. In low oxygen conditions this stage is not only achieved sooner than in the standard oxygen conditions (at a mechanical passage stage in 3 to 5 days after previous passage), but the cell populations are also more undifferentiated as shown by the increased expression of markers known to be associated with pluripotentiality and undifferentiation status of hESC e.g. October 4, (Peura et al. 2005, the disclosure of which is incorporated in its entirety herein by reference). The expression levels of these factors can be analysed with several different methods, including Polymerase Chain Reaction (PCR) (Zeng at al. 2004), cell sorting by flow cytometry (FACS) (Kim et al. 2004) and even whole genome DNA microarrays (Rao & Stice, 2004). Such monitoring techniques can be used in the large scale or automated procedures for quality control purposes thus further minimising the use of visual or other manual techniques.

Typically, in the actual passaging, the culture medium such as DMEM-KSR is first removed by aspiration with a vacuum pump or with a pipette and a pipettor or by decanting from the culture dishes, typically T75 or T175 culture flasks containing approximately 20 or 50 ml of medium, respectively. However, other types of dishes can be used, for example bioreactors containing microbeads kept in constant motion by magnetic stirrer (in which situation cells grow on the surfaces of the beads and the volume of medium depends on the size of bioreactor and the number of beads, to be determined separately for particular applications by simple trial and error or following standard laboratory manual, manufacturers recommendations and the like). Then cells are washed with $Ca^{++}$ and $Mg^{++}$-free PBS (Invitrogen), e.g. 5 ml to a T75-flask or 10 ml to a T175-flask. The selected cell dissociation reagent is then added and the dishes incubated on a warm stage or in an incubator. The volume of the reagent and the incubation time depends on the reagent, for example for Collagenase type IV 2.5 ml for T75-flask and 6 ml for T175-flask and 8-12 min incubation is used, but for Cell Dissociation Solution 5 ml for T75-flask and 10 ml for T175-flask and 5 min incubation may be more suitable.

After the incubation, at least the equal volume of the culture media is added to the dish and the cell layers are agitated with a pipette or a cell scraper or automatically on a vibrating platform to dislodge the cells. The cell suspension is then transferred to centrifuge tubes using either manual pipetting, or in a large scale application, an automated pipetting robot, and centrifuged at 1200 rpm for 4 min, the supernatant is discarded, and fresh culture media is added to the cells. The cells are then spilt to new culture dishes at 1:5 to 1:10 ratio, i.e. one dish yielding 5 to 10 new dishes, or cells equivalent to 1 $cm^2$ area on a dish being transferred to 5 to 10 $cm^2$ area in a new dish. The splitting ratio can be used to control when the next passage is to be done, Although it doesn't change the proliferation rate or the final cell numbers as such, the higher the ratio, the smaller number of cells will be transferred to a new dish and the longer they can be left to grow before they have utilised the available space in the dish. For expedient, efficient large scale cell expansion the splitting ratio can be quite high, as fewer passages in a given time require less labour. For example, one organ well culture dish (2.9 $cm^2$) with hESC colonies can be split roughly 1:10 by passaging cells to one T25-culture flask (25 $cm^2$). Using high splitting ratio, cells are passaged again in a similar manner every 6-10 days, this time to even bigger flasks (T75s or T175s, to 75 or 175 $cm^2$ growth areas, respectively).

The first goal in this example is to achieve enough cells for a Cell Master Bank, consisting of large number of cells (1-2× $10^7$) frozen at aliquots of (1-3×$10^6$ cells) at the same time from the same culture batch. Cryopreservation of hES cells is done with the same vitrification method used in Examples 4 and 6, with only small modification. Briefly, instead of cutting colonies mechanically, enzymatic or non-enzymatic cell dissociation method are used to prepare the colonies for vitrification. A representative sample of the cells is then subjected to detailed characterisation, sterility, differentiation ability and viability tests (as partially described in Examples 4 and 6), results of which then apply to the whole bank. From the Master Bank cells can be further expanded to downstream clinical and/or pharmacological applications.

The actual number of cells cultured in low oxygen increase between 2.8 to 7.7-fold during just one week of culture as compared with between 1.8 to 4.6 fold increase in cells grown in standard conditions. The actual level of increase depends on the exact passaging method, higher increase achieved with methods rendering the original colonies to smaller pieces, but this effect applies equally to both standard and low oxygen conditions. Cell expansion to a Master Bank level from a single 1-well organ culture dish will thus require several weeks less in low oxygen conditions as compared to standard conditions. Generally the shorter the time and less passages and population doublings are needed to achieve the Master Bank, the less likely is the accumulation of genetic instabilities or defects in the cells—especially if the increased cell proliferation is even partly due to reduced cell death. Hence achieving Master Bank in for example 6 weeks rather than 10 weeks is not only more effective and economical, it also aids in achieving a better outcome.

The methods described in this example are still relying on traditional two-dimensional culture methods, however, the advent of truly large-scale culture methods (Dang et al. 2004; Oh et al. 2005) and their application to the cell expansion can even further assist to increase the yield of cells even up to 5-32 fold. The basic advantage of the presently described low oxygen culture techniques and their effect on cell proliferation, and impact on method modifications, also apply to newer bioreactor-type large-scale culture methods. Use of such methodologies would make it even more feasible to achieve extraordinary quick and efficient production of hES cells for practical applications.

Although the invention has been described with reference to certain preferred embodiments, variations of the invention in keeping with its spirit and teaching are also within its scope.

REFERENCES

AlBadr M, Handyside A (2003): Derivation of trophectodermal stem cells from single blastomeres biopsied from cleavage stage mouse embryos. Proc 1st Nat Stem Cell Centre Sci Conf, 9-12, Oct. 2003, Melbourne, Australia, 5 (abstr.)

Amit M, Shariki C, Margulets V, Itskovitz-Eldor J. (2004a): Feeder layer- and serum-free culture of human embryonic stem cells. Biol Reprod. 70:837-845.

Amit M, Margulets, V, Sharik K, Itskovitz-Eldor J (2004b): Derivation of human embryonic stem cells harbouring genetic defects. ISSCR Pro. Int Soc Stem Cell Res Meeting, Jun. 10-13, 2004, Boston, p. 65 (abst.)

de Boer K A, Catt J W, Jansen R P, Leigh D, McArthur S. (2004) Moving to blastocyst biopsy for preimplantation genetic diagnosis and single embryo transfer at Sydney IVF. Fertil Steril 82:295-8.

Catt J, Henman M (2000): Toxic effects of oxygen on human embryo development. Hum Reprod 15:199-206.

Chung Y, Klimanskeya I, BeckerS, Marh J, Lu S, Johnson J, Meisner L, Lanza R (2005) Embryonic and extraembryonic stem cell lines derived from single mouse blastomeres Nature (advance online publication) doi:10.1038/nature04277

Cowan C A, Klimanskaya I, McMahon J, Atienza J. Witmyer J. Zucker J P, Wang S, Morton C C, McMahon A P, Powers D, Melton D A (2004) Derivation of embryonic stem-cell lines from human blastocysts. N Engl J Med 350: 1353-1356

Dang S M, Gerecht-Nir S. Chen J, Itskovitz-Eldor J, Zandstre P W (2004): Controlled, scalable embryonic stem cell differentiation culture. Stem Cells 22:275-283

Flechon J E, Laurie S, Notarianni E. (1995): Isolation and characterization of a feeder-dependent, porcine trophectoderm cell line obtained from a 9-day blastocyst. Placenta. 16: 643-658.

Galat V, Strelchenko N, Ozen S, Sky S, Kukharenko V, Verlinsky Y (2004): Human embryonic stem cells from embryos affected by genetic diseases. Proc. Int Soc Stem Cell Res Meeting, Jun. 10-13, 2004, Boston, p. 77 (abst.)

Geber S, Winston R M, Handyside A H (1995): Proliferation of blastomeres from biopsied cleavage stage human embryos in vitro: an alternative to blastocyst biopsy for preimplantation diagnosis. Hum Reprod. 110: 1492-1496.

Geber S. Sampaio M. (1999): Blastomere development after embryo biopsy: a new model to predict embryo development and to select for transfer. Hum Reprod. 14: 782-786.

Hogan B, Beddington R, Costantini F, Lacy E. (1994): Manipulating the Mouse Embryo: A Laboratory Manual, Cold Spring Harbor Laboratory Press, Cold Spring Harbor, N.Y. PP. 265-272

Hwang W S, Ryu Y J, Park J H, Park E S, Lee E G, Koo J M, Jeon H Y, Lee B C, Kang S K, Kim S J, Ahn C, Hwang J H, Park K Y, Cibelli J B, Moon S Y, (2004): Evidence of a pluripotent human embryonic stem cell line derived from a cloned blastocyst. Science. 303:1669-1674.

Hwang W S, Roh S I, Lee B C, Kang S K, Kwon D K, Kim S, Kim S J, Park S W, Kwon H S, Lee C K, Lee J B, Kim J M, Ahn C, Paek S H, Chang S S, Koo J J, Yoon H S, Hwang J H, Hwang Y Y, Park Y S, Oh S K, Kim H S, Park J H, Moon S Y, Schatten G. (2005) Patient-specific embryonic stem cells derived from human SCNT blastocysts. Science. 308 (5729):1777-1783.

Jansen R P S (2003): Female age and the chance of a baby from one in-vitro fertilisation treatment. Med J Aust 178; 258-261.

Kim S J, Park J H, Lee J E, Kim J M, Lee J B, Moon S Y, Roh S I, Kim C G, Yoon H S (2004): Effects of type IV collagen and laminin on the cryopreservation of human embryonic stem cells. Stem Cells 22:950961

Leoni G, Ledda S, Bogliolo L, Naitana S (2000): Novel approach to cell sampling from preimplantation ovine embryos and its potential use in embryonic genome analysis. J Reprod Fertil 119: 309-314.

McArthur S J, Leigh D, Marshall J T, de Boer K A, Jansen R P S (2005): Pregnancies and live births after trophectoderm biopsy and preimplantation genetic testing of human blastocysts. Fertil, Steril. (in press).

Oh S K, Fong W J, Teo Y, Tan H L, Padmanabhan J. Chin A C, Choo A B (2005): High density cultures of embryonic stem cells. Biotechnol Bioeng 91:523-33

Orsi N M, Leese H J (2001): Protection against reactive oxygen species during mouse preimplantation embryo development: role of EDTA, oxygen tension, catalase, superoxide dismutase and pyruvate. Mol Reprod Dev 59: 44-53.

Pedersen R A (1994): Studies of in vitro differentiation with embryonic stem cells. Reprod Fertil Dev. 6:543-52. (Review)

Pedersen, R A (1999) Embryonic stem cells for medicine. Sci Am. 280:68-73.

Peura T, Bosman A, Leigh D, Curley B, Schaft t, Stojanov T, Chami O (2005): Reduced Oxygen Atmosphere Affects Gene Expression in Human Embryonic Stem Cells as Analysed by Whole Genome Microarrays. Proc. 3rd Australian Stem Cell Centre Conf., Gold Coast, November 6-9, 2005, abst. 128.

Rao R R, Stice S L (2004): Gene expression profiling of embryonic stem cells leads to greater understanding of pluripotency and early developmental events. Biol Reprod 71:1772-1778

Reubinoff B E, Pera M F, Fong C Y, Trounson A, Bongso A. (2000): Embryonic stem cell lines from human blastocysts: somatic differentiation in vitro. Nat Biotechnol. 18:309404

Reubinoff B E, Pera M F, Vajta G., Trounson A O. (2001): Effective cryopreservation of human embryonic stem cells by the open pulled straw vitrification method. Hum Reprod. 16(10):2187-2194

Robertson, Meth. Cell Biol. 75:173, 1997

Shimada A, Nakano K, Takahashi T, Imal K, Hashizume K. (2001): Isolation and characterization of a bovine blastocyst-derived trophoblastic cell line, BT-1: development of a culture system in the absence of feeder cell, Placenta. 22: 652-662.

Solter D, Knowles B B (1975) Immunosurgery of mouse blastocyst. Proc Natl Acad Sci USA 72: 5099-5102.

van Stekelenburg-Hamers A E, Van Achterberg T A, Rebel H G, Flechon J E, Campbell K H, Weima S M, Mummery C L. (1995): Isolation and characterization of permanent cell lines from inner cell mass cells of bovine blastocysts. Mol Reprod Dev. 40:444-464.

van de Stolpe A, van den Brink S, van Rooijen M, Ward-van Oostwaard D, van Inzen W, Slaper-Cortenbach I, Fauser B C J M, den van den Hout N, Weima S S, Passier R, Smith N, Denning C, Mummery C: Human embryonic stem cells: towards therapies for cardiac disease. Derivation of a Dutch human embryonic stem cell line. RBMOnline 11: 476-485

Talbot N C, Caperna T J, Edwards J L, Garrett W. Wells K D, Ealy A D. (2000): Bovine blastocyst-derived trophectodern and endoderm cell cultures: interferon tau and transferrin expression as respective in vitro markers. Biol Reprod. 62: 235-247.

Tanaka S, Kunath T, Hadjantonakis A K, Nagy A, Rossant J. (1998): Promotion of trophoblast stem cell proliferation by FGF4 Science. 282: 2072-2075.

Thomson J A, Kalishman J, Globs T G, Durning M, Harris G P, Becker R A, Hearn, J P (1995): Isolation of a primate embryonic stem cell line. Proc. Natl. Acad. Sol. USA 92:7811-7848

Thomson J A, Itskovitz-Eldor J, Shapiro S S, Waknitz M A, Swiergiel J J, Marshall V S, Jones J M. (1998) Embryonic stem cell lines derived from human blastcysts. Science. 282:1445-1147.

Vajta G, Kuwayanma M, Holm P, Booth P, Jacobsen H, Greve T, Callesen H (1998): A new way to avoid cryoinjuries of mammalian ova and embryos: the OPS-vitrification. Mol Reprod Dev 51, 53-58

Verlinssky Y, Strelchenko N, Kukharenko V, Galat V (2004): Preimplantation genetic diagnosis: as a source of human embryonic stem cell lines. Proc. Int Soc Stem Cell Res Meeting, Jun. 10-13, 2004, Boston, p. 166 (abst.)

Zeng X, Miura T, Luo Y, Bhattacharya B, Condie B, Chen J, Ginis I, Lyons I, Mejido J. Puri R K, Rao M S, Freed W J (2004): Properties of pluripotent human embryonic stem cells BG01 and BG02. Stem Cells 22:292-31

The invention claimed is:

1. A method of derivation of embryo-derived cells or embryo-derived cell lines consisting of the following steps:
   a) culturing an embryo under low oxygen tension conditions of about 5% oxygen to the blastocyst stage;

b) separating Inner Cell Mass (ICM) cells of said blastocyst from trophectodermal cells, plating said ICM cells and culturing said ICM cells under low oxygen tension conditions of about 5% oxygen for a time sufficient to produce embryonic cell-like outgrowths;

c) at least once, dissociating said embryonic cell-like outgrowths, replating said dissociated embryonic cell-like outgrowths and culturing said dissociated embryonic cell-like outgrowths under low oxygen tension conditions of about 5% oxygen for a time sufficient to produce further embryonic cell-like outgrowths;

d) analyzing said further embryonic cell-like outgrowths of step c) for embryonic stem cell-like properties;

e) selecting outgrowths with embryonic stem cell-like properties; and f) isolating and dissociating said outgrowths with embryonic stem cell-like properties selected in step e) and culturing the dissociated cells under low oxygen tension conditions of about 5% oxygen to obtain embryo-derived cells or embryo-derived cell lines.

2. A method of derivation of embryo-derived cells or embryo-derived cell lines consisting of the following steps:

a) incubating a putative zygote in a culture medium under low oxygen tension conditions of about 5% oxygen to derive an embryo;

b) culturing embryo obtained in step a) under low oxygen tension conditions of about 5% oxygen to the blastocyst stage;

c) separating Inner Cell Mass (ICM) cells of said blastocyst from trophectodermal cells, plating said ICM cells and culturing said ICM cells under low oxygen tension conditions of about 5% oxygen for a time sufficient to produce embryonic cell-like outgrowths;

d) at least once, dissociating said embryonic cell-like outgrowths, replating said dissociated embryonic cell-like outgrowths and culturing said dissociated embryonic cell-like outgrowths under low oxygen tension conditions of about 5% oxygen for a time sufficient to produce further embryonic cell-like outgrowths;

e) analyzing said further embryonic cell-like outgrowths of step d) for embryonic stem cell-like properties;

f) selecting outgrowths with embryonic stem cell-like properties;

g) isolating and dissociating said outgrowths with embryonic stem cell-like properties selected in step f) and culturing the dissociated cells under low oxygen tension conditions of about 5% oxygen to obtain embryo-derived cells or embryo-derived cell lines.

3. The method according to claim 1 or 2, wherein the embryo-derived cell or embryo-derived cell line is a stem cell or stem cell line.

* * * * *